(12) United States Patent
Moberg et al.

(10) Patent No.: US 11,484,648 B2
(45) Date of Patent: Nov. 1, 2022

(54) DRUG DELIVERY DEVICE WITH CONTAINER ACCESS SYSTEM AND RELATED METHOD OF ASSEMBLY

(71) Applicant: AMGEN INC., Thousand Oaks, CA (US)

(72) Inventors: Sheldon Moberg, Thousand Oaks, CA (US); Matthew Wayne Janke, Simi Valley, CA (US); Wael Mismar, Redondo Beach, CA (US); Alexis Dechelette, Jenkintown, PA (US)

(73) Assignee: AMGEN INC., Thousand Oaks, CA (US)

( * ) Notice: Subject to any disclaimer, the term of this patent is extended or adjusted under 35 U.S.C. 154(b) by 160 days.

(21) Appl. No.: 16/625,208

(22) PCT Filed: Jul. 11, 2018

(86) PCT No.: PCT/US2018/041564
§ 371 (c)(1),
(2) Date: Dec. 20, 2019

(87) PCT Pub. No.: WO2019/022950
PCT Pub. Date: Jan. 31, 2019

(65) Prior Publication Data
US 2021/0330880 A1    Oct. 28, 2021

Related U.S. Application Data

(60) Provisional application No. 62/536,909, filed on Jul. 25, 2017.

(51) Int. Cl.
*A61M 5/162* (2006.01)
*A61M 5/142* (2006.01)
*A61M 5/20* (2006.01)

(52) U.S. Cl.
CPC ........ *A61M 5/162* (2013.01); *A61M 5/14248* (2013.01); *A61M 5/2033* (2013.01);
(Continued)

(58) Field of Classification Search
CPC .............. A61M 5/162; A61M 5/14248; A61M 5/2033; A61M 2005/14252;
(Continued)

(56) References Cited

U.S. PATENT DOCUMENTS 3,336,924 A * 8/1967 Sarnoff ................. A61J 1/2096
206/229
5,330,426 A    7/1994 Kriesel et al.
(Continued)

FOREIGN PATENT DOCUMENTS

JP    2015513440 A    5/2015
WO   WO-9403373 A1 *  2/1994  ............ A61J 1/1406
(Continued)

OTHER PUBLICATIONS

Written Opinion of International Application No. PCT/US2018/041564, dated Sep. 20, 2018.
International Search Report of International Application No. PCT/US2018/041564, dated Sep. 20, 2018.
Japanese Patent Application No. 2019-566891, Notice of Rejection, dated May 31, 2022.

*Primary Examiner* — Jason E Flick
(74) *Attorney, Agent, or Firm* — Marshall, Gerstein & Borun LLP

(57) ABSTRACT

Drug delivery devices and related methods of assembly are disclosed. The drug delivery device may include a container including a wall with an interior surface and a seal member with an end surface. The interior surface of the wall and the end surface of the seal member may define a reservoir filled with a drug. A fluid pathway assembly may be connected to the container and include an overmold member that covers a length of a container access needle and which defines an enclosed space with the seal member. The overmold member
(Continued)

may be moveable relative to the seal member to carry the container access needle between a storage position, where a point of the container access needle is disposed exterior to the reservoir, and a delivery position, where the point extends through the end surface of the seal member into the reservoir.

22 Claims, 4 Drawing Sheets

(52) U.S. Cl.
CPC ............. *A61M 2005/14252* (2013.01); *A61M 2207/00* (2013.01); *A61M 2209/045* (2013.01)

(58) Field of Classification Search
CPC .......... A61M 2209/045; A61M 5/2466; A61M 5/288; A61M 39/18; A61M 2207/00; A61M 2207/10; A61M 5/20; A61M 5/14; A61M 5/142; A61M 5/14244; A61M 2005/206; A61M 5/2455; A61M 5/285

See application file for complete search history.

(56) References Cited

U.S. PATENT DOCUMENTS

| 11,033,679 | B2 | 6/2021 | Hanson et al. |
| 2014/0200510 | A1 | 7/2014 | Agard et al. |
| 2014/0213975 | A1* | 7/2014 | Clemente .......... A61M 5/14248 604/151 |
| 2014/0336586 | A1* | 11/2014 | Bengtsson .......... A61M 5/2466 604/218 |
| 2015/0073353 | A1* | 3/2015 | Strader ................... A61L 2/081 29/434 |

FOREIGN PATENT DOCUMENTS

| WO | WO-2012158136 | A1 | 11/2012 | |
| WO | WO-2016141082 | A1 | 9/2016 | |
| WO | WO-2016145206 | A1 | 9/2016 | |
| WO | WO-2017009640 | A1 * | 1/2017 | ................ A61J 1/06 |
| WO | WO-2017089270 | A1 | 6/2017 | |

* cited by examiner

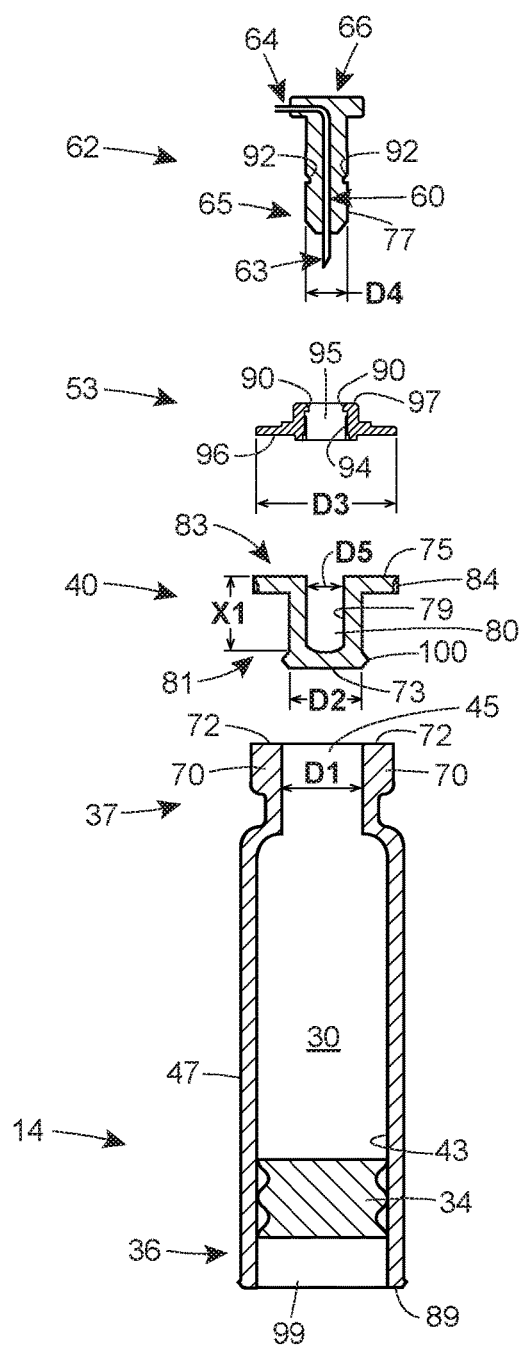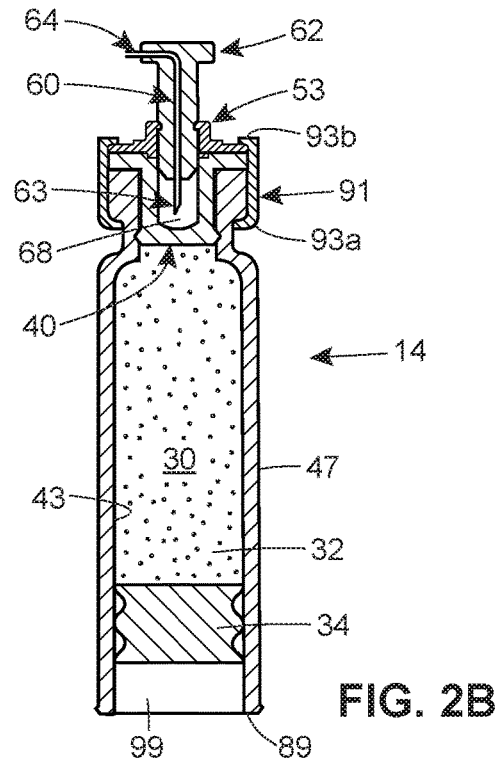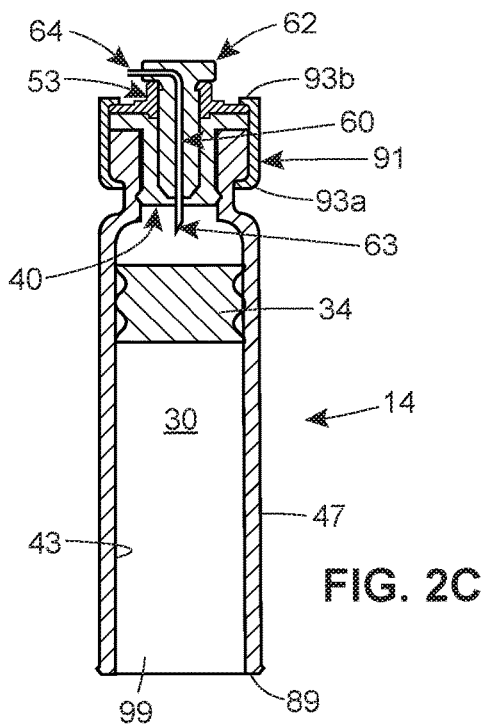
FIG. 2A
FIG. 2B
FIG. 2C

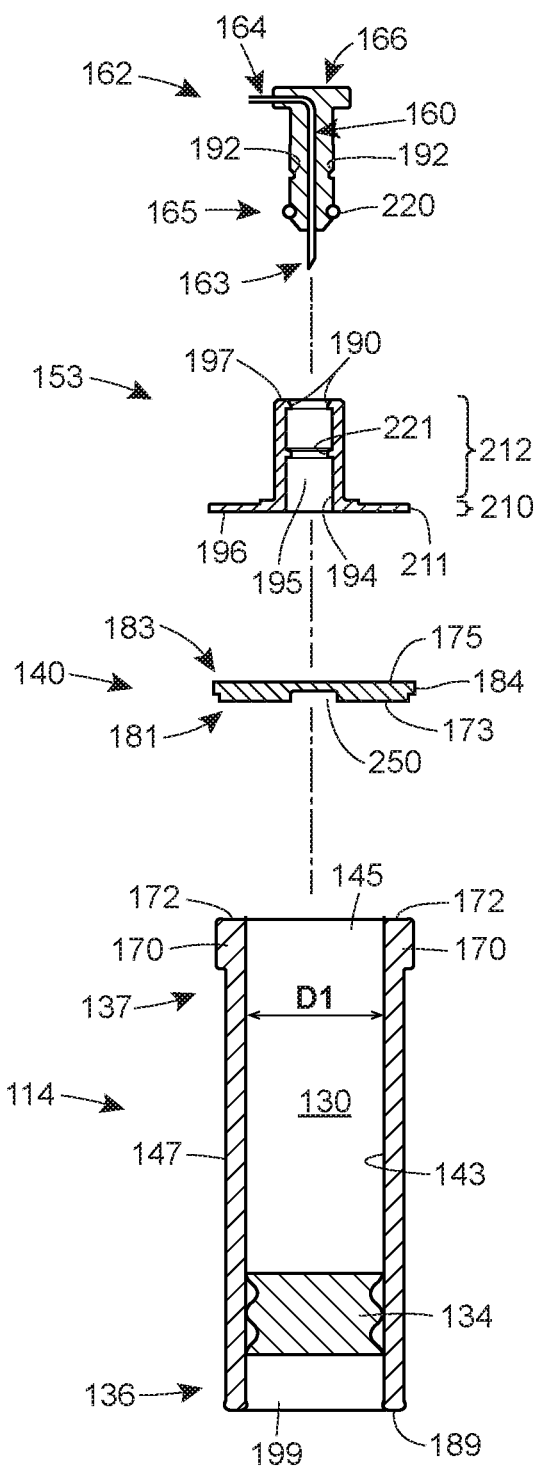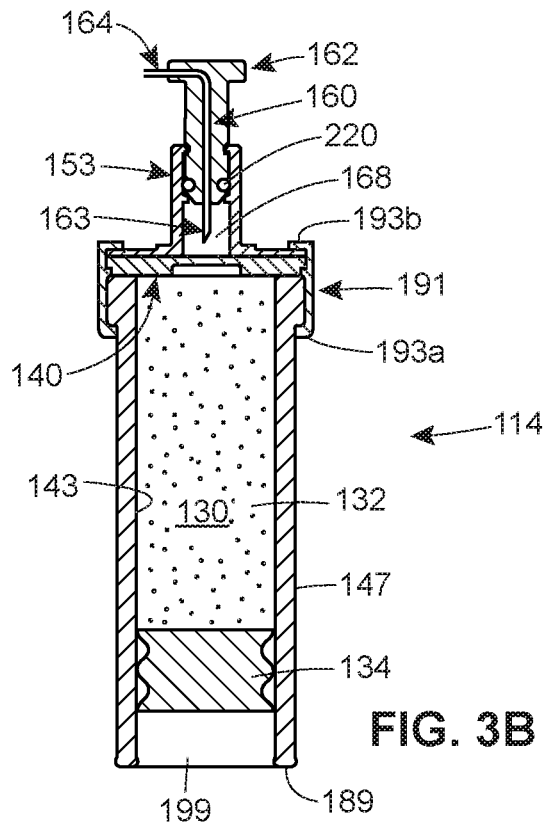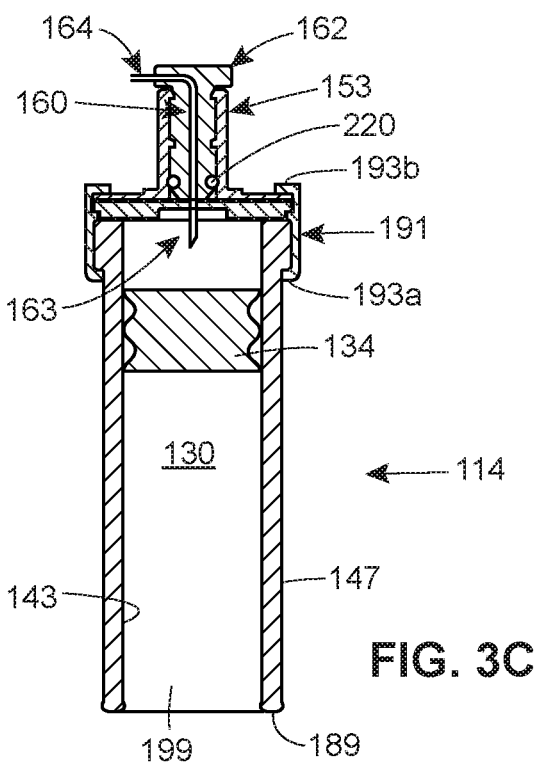
FIG. 3A
FIG. 3B
FIG. 3C

DRUG DELIVERY DEVICE WITH CONTAINER ACCESS SYSTEM AND RELATED METHOD OF ASSEMBLY

CROSS-REFERENCE TO RELATED APPLICATION

This is the United States National Phase of PCT/US2018/041564, filed Jul. 11, 2018, which claims the priority benefit of U.S. Provisional Patent Application No. 62/536,909, filed Jul. 25, 2017, the entire contents of each of which are hereby incorporated herein by reference.

FIELD OF DISCLOSURE

The present disclosure generally relates to drug delivery devices and more particularly, but not necessarily exclusively, enabling a sterile fluid flow path between a drug container assembled within a drug delivery device and a patient.

BACKGROUND

Drug delivery devices, such as injectors, are used to deliver liquid drugs to a patient. Upon activation, a drug delivery device will expel a drug stored within an internal reservoir through a needle, cannula, or other delivery member into the patient. Certain drug delivery devices are manufactured with an empty reservoir, and the patient or healthcare provider (e.g., a doctor, nurse, healthcare assistant, etc.) will fill the reservoir with the drug at the time of use. Typically this requires the patient or healthcare provider to operate a syringe to inject the drug into the empty reservoir through an inlet port formed in the drug delivery device. Prior to this filling procedure, the inlet port should be sterilized by swabbing its outer surface with an alcohol wipe, for example. Alternatively, certain drug delivery devices are installed with a pre-filled drug container by the patient or healthcare provider at the time of use. Before installing the pre-filled drug container, mating connectors disposed on, respectively, the pre-filled drug container and a fluid pathway assembly within the device should be sterilized, for example, by swabbing them with an alcohol wipe. In either case, the drug delivery device must be prepared by the patient or healthcare provider prior to use.

More recently, drug delivery devices have become available which are pre-assembled with a pre-filled drug container. This alleviates the patient or healthcare provider from having to add the drug to the drug delivery device at the time of treatment. In such drug delivery devices, a sterile fluid flow path is established between the pre-filled drug container and a fluid pathway assembly upon activation of the device. Generally this involves accessing an interior of the drug container with a container access needle such that the drug can be expelled from the container via the container access needle. Prior to activation of the device, the container access needle should be maintained in a sterile condition so that the container access needle does not introduce contaminants into the container upon activation of the device. Existing assemblies for enabling sterile access of the drug container via the container access needle tend to be bulky, difficult to assemble, and/or overly complex in design.

The present disclosure sets forth drug delivery devices and related methods of assembly embodying advantageous alternatives to existing drug delivery devices and methods of assembly, and that may address one or more of the challenges or needs mentioned herein, as well as provide other benefits and advantages.

SUMMARY

One aspect of the present disclosure provides a drug delivery device including a container, a seal member, and a fluid pathway assembly connected to the container. The container may have a wall with an interior surface and the seal member may have an end surface. The interior surface of the wall and the end surface of the seal member may define a reservoir filled with a drug. The fluid pathway assembly may include a container access needle having a point, and an overmold member. The overmold member may cover a length of the container access needle and define an enclosed space between the overmold member and the seal member. The overmold member may be moveable relative to the seal member to carry the container access needle between a storage position, where the point of the container access needle is disposed exterior to the reservoir, and a delivery position, where the point of the container access needle extends through the end surface of the seal member into the reservoir.

Another aspect of the present disclosure provides a method of assembly, including: (a) providing a container having a wall with an interior surface and, a fluid pathway assembly including a container access needle having a point and an overmold member covering a length of the container access needle with the point protruding outwardly from the overmold member; (b) covering a first opening formed in the wall of the container with a seal member such that an end surface of the seal member and the interior surface of the wall of the container define a reservoir; and (c) positioning the overmold member to define an enclosed space between the overmold member and the seal member.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

FIG. 2A depicts cross-sectional exploded view of a container, a seal member, and a fluid pathway assembly depicted in FIG. 1.

FIG. 2B illustrates a cross-sectional assembled view of a storage state of the container, seal member, and fluid pathway assembly illustrated in FIG. 2A.

FIG. 2C illustrates a cross-sectional assembled view of a delivery state of the container, seal member, and fluid pathway assembly illustrated in FIG. 2A.

FIG. 3A depicts cross-sectional exploded view of another embodiment of a container, seal member, and fluid pathway assembly.

FIG. 3B illustrates a cross-sectional assembled view of a storage state of the container, seal member, and fluid pathway assembly illustrated in FIG. 3A.

FIG. 3C illustrates a cross-sectional assembled view of a delivery state of the container, seal member, and fluid pathway assembly illustrated in FIG. 3A.

DETAILED DESCRIPTION

The present disclosure generally relates to a sterile fluid flow path between a drug container assembled within a drug delivery device and a patient. The drug delivery device may include a fluid pathway assembly that, in response to activation of the device or a control signal, establishes fluid communication between a reservoir of the drug container and other components or assemblies of the device. Prior to activation, a container access needle of the fluid pathway assembly may be disposed exterior to the reservoir. Upon activation, a point of the container access needle may be inserted through a seal member, such as a pierceable septum, to provide fluid communication with a drug in the reservoir. If microbes or other contaminants are disposed on the point of the container access needle, the container access needle may introduce contaminants into the reservoir. In order to reduce the possibility of such contamination, certain embodiments of the present disclosure store the point of the container access needle in an enclosed clean space prior to activation of the drug delivery device. The enclosed clean space may be defined between the seal member and an overmold member covering a length of the container access needle. In some embodiments, the overmold member may be received within a recess formed in the seal member to define the enclosed clean space. In other embodiments, the overmold member may be received within an interior of an annular clip member mounted on the seal member in order to define the enclosed clean space. Utilizing the overmold member to create the enclosed clean space may facilitate a more compact design of the fluid pathway assembly, which in turn may permit a smaller overall size of the drug delivery device. Furthermore, the relative simplicity of this design may improve the manufacturability of the drug delivery device, among other advantages.

Each of the foregoing components of the drug delivery device and methods of assembling such a device will now be described in more detail.

Figure 1:
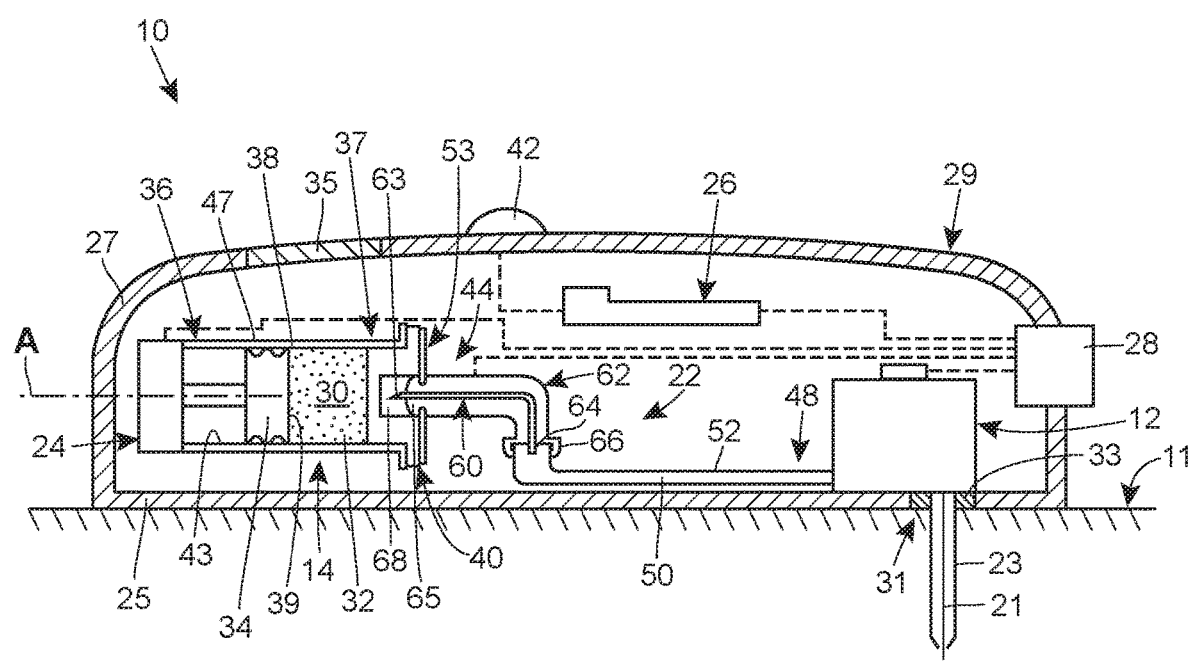
FIG. 1 illustrates a schematic cross-sectional view of an embodiment of a drug delivery device in accordance with principles of the present disclosure.

FIG. 1 is a schematic illustration of one embodiment of a drug delivery device 10 constructed in accordance with principles of the present disclosure. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, and is releasably attachable to the patient's tissue 11 (e.g., the patient's skin). In other embodiments (not illustrated), the drug delivery device 10 may be configured as a pen-type injector, such as an autoinjector or injection pen, which is temporarily held against the patient's tissue 11 over the course of the injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional or other caregiver to administer the injection.

Generally, the drug delivery device 10 may include an insertion mechanism 12, a container 14, a fluid pathway assembly 22, a drive mechanism 24, and a controller 26, each of which may be disposed within an interior space of a main housing 29. An actuator 28 (e.g., a user-depressible button, touchscreen, microphone, etc.) may protrude through or otherwise be disposed at an exterior surface of the housing 29 and may be configured to initiate operation of the drug delivery device 10 by activating, via mechanical and/or electrical means (shown in dotted lines in FIG. 1), the insertion mechanism 12, the fluid pathway assembly 22, the drive mechanism 24, the controller 26, and/or other mechanisms and/or electronics. In embodiments where the actuator 28 is a button that is depressed or otherwise physically moved by a user or patient, the actuator 28 may be configured to exert a motive force needed to activate the insertion mechanism 12, the fluid pathway assembly 22, the drive assembly 24, the controller 26, and/or other mechanisms. In such embodiments, the actuator 28 may be physically connected to, either directly or indirectly via a mechanical linkage, the insertion mechanism 12, the drive mechanism 24, the fluid pathway assembly 22, and/or other mechanisms such that manually depressing or otherwise interacting with the actuator 28 supplies the motive force necessary to activate the insertion mechanism 12, the drive mechanism 24, the fluid pathway assembly 22, and/or other mechanisms. For example, in some embodiments, manually depressing the actuator 28 may cause the fluid pathway assembly 22 to move towards the stationary container 14, or cause the container 14 to move towards the stationary fluid pathway assembly 22, and thereby cause a container access needle to penetrate through a seal member into a reservoir or interior volume of the container 14. Additionally or alternatively, the actuator 28 may operate as an input device that transmits an electrical and/or mechanical signal to the controller 26, which in turn may execute programmable instructions to control operation of the insertion mechanism 12, the drive mechanism 24, the fluid pathway assembly 22, and/or other mechanisms. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 28 and which, in response to an electrical control signal received from the controller 26, exerts the motive force needed to activate the insertion mechanism 12, the drive mechanism 24, the fluid pathway assembly 22, and/or other mechanisms.

Still referring to FIG. 1, the housing 29 may include a bottom wall 25 configured to be releasably attached (e.g., adhered with an adhesive) to the patient's tissue 11, and a top wall 27 including one or more visual indicators 42 (e.g., lights, graphical displays, etc.) and/or a window 35 for viewing the container 14 and a drug 32 contained therein. The one or more visual indicators 42 may be used to communicate information to the user about the operational state of the drug delivery device 10 and/or the condition of the drug 32. An opening 31 may be formed in the bottom wall 25, and optionally a pierceable sterile barrier 33, such as a pierceable septum, may extend across the opening 31 to seal the interior of the housing 29 prior to use. In some embodiments, the pierceable sterile barrier 33 may be omitted, and instead a removable sealing member (not illustrated) may cover and seal close the opening 31 prior to use.

More particularly with respect to the window 35, this element may be constructed of a transparent or semi-transparent material and generally aligned with the container 14, so as to allow a patient or user of the drug delivery device 10 to inspect the drug 32 within the container 14 and/or confirm dose completion. Suitable materials for constructing the window 35 include, but are not limited to, glass and/or plastic. The location of the window 35 on the exterior of the drug delivery device 10 may expose the drug 32 to ambient light including sunlight. Some drugs may be sensitive to certain wavelengths of light and undergo undesirable molecular changes when exposed to such wavelengths of light. For example, some drugs may be sensitive to wavelengths of light in the ultraviolet (UV) range, the visible range, and/or the infrared range. To protect drugs that are primarily sensitive to light in the UV range and/or the infrared range, a dark tint may be added to the window 35 and/or the window 35 may be dimensioned to cover a relatively small surface area of the housing 29. For drugs that are primarily sensitive to light in the visible range, it may not be necessary to add a dark tint to the window 35 and/or shrink the size of the window 35. Instead, the window 35 may be constructed with a polarized filter. In some embodiments, the polarized filter may be a film or other coating that is applied to the window 35. In other embodiments, the polarized filter may be integrated directly into the material of window 35. The polarized filter may allow for viewing and inspection of the drug 32 within the container 14, while filtering out up to and including approximately (e.g., ±10%) 50% of light in the visible range. In some embodiments, the portion of visible light filtered out by the window 35 may fall in a range between approximately (e.g., ±10%) 0-50%, or 10-50%, or 20-50%, or 25-50%, or 0-40%, or 0-30%, or 0-25%, depending on the photosensitivity of the drug 32 and/or the eye strength of the patient population of the drug 32, among other considerations. Adding the polarized filter to the window 35, in lieu adding a dark tint to the window 35 and/or shrinking the size of the window 35, advantageously protects the drug 35 from light in the visible range without substantially compromising the ability of the patient or user of the drug delivery device 10 to inspect the drug 32 within the container 14.

After the bottom wall 25 of the housing 29 is attached to the patient's tissue 13, the insertion mechanism 12 may be activated to move a delivery member from a retracted position within the housing 29 to a deployed position extending outside of the housing 29. In the present embodiment, this may include the insertion mechanism 12 inserting a trocar 21 and a hollow cannula 23 surrounding the trocar 21 through the pierceable sterile barrier 33 and into the patient's tissue 11, as illustrated in FIG. 1. Immediately or shortly thereafter, the insertion mechanism 12 may automatically retract the trocar 21, leaving the distal open end of the cannula 23 inside the patient for subcutaneous delivery of the drug 32. The trocar 21 may be solid and have a sharpened end for piercing the patient's skin 11. Furthermore, the trocar 21 may be made of a material that is more rigid than the cannula 23. In some embodiments, the trocar 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient. In other embodiments (not illustrated), the trocar 21 and cannula 23 may be omitted, and instead the insertion mechanism 12 may insert only a rigid, hollow needle into the patient for subcutaneous delivery of the drug 32.

In some embodiments, the insertion mechanism 12 may include one or more springs (e.g., coil springs, torsion springs, etc.) initially retained in an energized state, and which are released upon depression of the actuator 28 in order to insert the trocar 21 and cannula 23, or hollow needle, into the patient. Furthermore, retraction of the trocar 21 may be achieved by the automatic release of another spring after the trocar 21 and cannula 23 have been inserted into the patient. Other power sources for insertion and/or retraction are possible, including, for example, an electric motor, a hydraulic or pneumatic pump, or a canister that releases a pressurized gas or pressurized liquid to provide actuation energy.

With continued reference to FIG. 1, the container 14, which in some contexts may be referred to as a primary container, may include a wall 38 with an interior surface 43 defining a reservoir 30 that is filled with the drug 32 and an exterior surface 47. In some embodiments, the reservoir 30 may be pre-filled with the drug 32 by a drug manufacturer prior to installation of the container 14 in the drug delivery device 10. In some embodiments, the container 14 may be rigidly connected to the housing 29 such that the container 14 cannot move relative to the housing; whereas, in other embodiments, the container 14 may be slidably connected to the housing 29 such that the container 14 can move relative to the housing 29 during operation of the drug delivery device 10. The container 14 may have an elongate, barrel-like or cylindrical shape extending along a longitudinal axis A. In embodiments where the drug delivery device 10 is configured as an on-body injector, the longitudinal axis A of the container 14 may be perpendicular or substantially perpendicular, or otherwise non-parallel, to a direction in which the insertion mechanism 12 inserts a delivery member such as the cannula 23 into the patient. This configuration may allow the on-body injector to have a generally planar, low-profile shape that can be worn by the patient without impeding the patient's movement. Initially, a stopper 34 or other piston member may be positioned in the reservoir 30 at a proximal end 36 of the container 14. The stopper 34 may sealingly and slidably engage the interior surface 43 of the wall 38 of the container 14, and may be movable relative to the wall 38 of the container 14.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL. The reservoir 30 may be completely or partially filled with the drug 32. The drug 32 may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive mechanism 24 may push the stopper 34 along the longitudinal axis A from the proximal end 36 of the container 14 to a distal end 37 of the container 14 in order to expel the drug 32 from the container 14. In some embodiments, the drive mechanism 24 may include one or more springs (e.g., coil springs, torsion springs, etc.) initially retained in an energized state, and which are released upon depression of the actuator 28. Following their release, the spring(s) may expand or contract to move the stopper 34 through the reservoir 30 along the longitudinal axis A from the proximal end 36 of the container 14 to the distal end 37 of the container 14. In other embodiments, the drive mechanism 24 may include an electric motor (not illustrated) which rotates a gear mechanism, including for example one or more sprocket gears, to cause axial motion of the stopper 34 through the reservoir 30. In still further embodiments, the drive mechanism 24 may include both an electric motor and spring(s), wherein the electric motor regulates expansion of the spring(s) via a tether or pulley system. In still further embodiments, the drive mechanism 24 may include a canister that releases a pressurized gas or pressurized liquid to provide actuation energy.

At the distal end 37 of the container 14, an opening 45 (see FIG. 2A) may be formed in a distal end surface 72 (see FIG. 2A) of the wall 38. The distal end surface 72 may define a portion of the exterior surface 47 of the wall 38. At least prior to operation of the drug delivery device 10, the opening 45 may be covered and sealed closed by a seal member 40, such as a pierceable septum, connected to the distal end 37 of the container 14. The seal member 40 may include a proximal end surface 73 and a distal end surface 75. The proximal end surface 73 of the seal member 40 and the interior surface 43 of the wall 38 of the container 14 may define the reservoir 30. Additionally, in some embodiments, a distal end surface 39 of the stopper 34 may define the reservoir 30.

Generally, the seal member 40 may be configured to selectively permit access to the reservoir 30. During operation, the seal member 40 may be physically altered (e.g., pierced) to permit fluid communication with the drug 32 in the reservoir 30. In some embodiments, the seal member 40 may be constructed of a flexible or elastically deformable material such as rubber, for example, which is capable of being penetrated or pierced by a sharpened end or point 63 of a container access needle 60 of the fluid pathway assembly 22. In some embodiments, the seal member 40 may be clamped or otherwise secured to the distal end surface 72 of the wall 38 by a fastener 91 (see FIGS. 2B and 2C) and/or adhered directly to the distal end surface 72.

Still referring to FIG. 1, the fluid pathway assembly 22 may be configured to establish fluid communication between the container 14 and the insertion mechanism 12 via a sterile fluid flow path during operation of the drug delivery device 10. Prior to use of the drug delivery device 10, the fluid pathway assembly 22 may not be in fluid communication with the container 14. During setup of the drug delivery device 10, or during the initial stages of operation of the drug delivery device 10 prior to drug delivery, the user may manually, or the drug delivery device 10 may automatically, enable, connect, or open the necessary connections to establish fluid communication between the container 14 and the fluid pathway assembly 22. Subsequently, the drive mechanism 24 may move the stopper 34 in the distal direction to force the drug 32 stored in the container 14 through the sterile fluid flow path of the fluid pathway assembly 22 and into the cannula 23 or needle or other delivery member of the insertion mechanism 12 for subcutaneous delivery to the patient.

In some embodiments, the fluid pathway assembly 22 may be rigidly connected to the housing 29 such that the fluid pathway assembly 22 cannot move relative to the housing; whereas, in other embodiments, the fluid pathway assembly 22 may be slidably or moveably connected to the housing 29 such that the fluid pathway assembly 22 can move relative to the housing 29 during operation of the drug delivery device 10. In the former embodiments, the container 14 may be slidably or moveably connected to the housing 29 and such that the seal member 40 can be moved toward and pierced by the point 63 of the stationarily arranged container access needle 60 of the fluid pathway assembly 22. In the latter embodiments, the container 14 may be stationarily positioned while the fluid pathway assembly 22 is moved toward the container 14, causing the point 63 of the container access needle 60 to pierce through the seal member 40 and access the reservoir 30.

The fluid pathway assembly 22 may include a first end 44 connected to the container 14, a second end 48 connected to the insertion mechanism 12, and a fluid passage 50 extending between the first end 44 and the second end 48. As described in more detail below, in some embodiments the first end 44 of the fluid pathway assembly 22 may be connected to the container 14 via a clip member 53. The fluid passage 50 may be sterilized, and may be partially or entirely made of a flexible tubing 52. Initially, there may be slack in the flexible tubing 52 to allow the fluid pathway assembly 22 to move relative to the housing 29 and/or to allow components of the insertion mechanism 12 to which the fluid pathway assembly 22 is attached to move relative to the housing 29. In some embodiments, the fluid passage 50 may include a rigid fluid restrictor element (not illustrated) in addition to the flexible tubing 52. The fluid restrictor element may have a smaller inner diameter than that of the flexible tubing 52 in order to regulate the flow rate of the drug 32 as it passes through the fluid pathway assembly 22. Furthermore, the fluid restrictor element may be made of a more rigid material than the flexible tubing 52. For example, the fluid restrictor element made be made of metal, whereas the flexible tubing 52 may be made of a polymeric material such as plastic.

Still referring to FIG. 1, the first end 44 of the fluid pathway assembly 22 may include the container access needle 60 and an overmold member 62. In general, the overmold member 62 may serve as a mounting member or connection hub for the container access needle 60 and provide a portion of the container access needle 60 which does not access the reservoir 30 with an enlarged outer dimension, such as an enlarged outer diameter. The container access needle 60 may have a sharpened end or point 63, corresponding to a proximal end of the container access needle 60, and a distal end 64 in fluid communication with the fluid passage 50. In the illustrated embodiment, the container access needle 60 has a bend such that the point 63 of the container access needle 60 may be axially aligned with the longitudinal axis A of the container 14 whereas the distal end 64 of the container access needle 60 may be perpendicular or otherwise non-parallel to the longitudinal axis A of the container 14. The overmold member 62 may cover a length of the container access needle 60, including the bend, with the point 63 of the container access needle 60 protruding outwardly from a proximal end 65 of the overmold member 62. As shown in FIG. 1, a distal end 66 of the overmold member 62 may include a mouth or opening that allows an end of the flexible tubing 52 to be inserted into the overmold member 62. In alternative embodiments, the distal end 66 of the overmold member 62 may be inserted into an opening formed in the end of the flexible tubing 52.

The container access needle 60 may possess a hollow, tubular shape with one or more openings at each of the point 63 and the distal end 64. The container access needle 60 made be constructed of a rigid material including, but not limited to, metal (e.g., stainless steel) and/or plastic. In some embodiments, the overmold member 62 may be constructed of a different material than the container access needle 60 such that the overmold member 62 and the container access needle 60 are separate, but rigidly connected, components. In some embodiments, the overmold member 62 may be constructed of a rigid plastic material whereas the container access needle 60 is constructed of metal. In other embodiments, the overmold member 62 and the container access needle 60 may be made of the same material such that they form a single, unitary one-piece structure.

Generally, the overmold member 62 may have a sleeve-like or tubular shape that surrounds a length of the container access needle 60. The overmold member 62 may be fixedly or rigidly connected to the needle 60 such that the overmold member 62 and the needle 60 can move together jointly as a single unit or structure. Stated another way, the overmold member 62 may be fixedly or rigidly connected to the container access needle 60 such that the needle 60 is prevented from moving relative to the overmold member 62. In some embodiments, the fixed or rigid connection between the overmold member 62 and the container access needle 60 may be achieved by having the material of the overmold member 62 bond to the material of the container access needle 60. Such bonding may be achieved by forming the overmold member 62 around the container access needle 60 by way of an overmolding or insert molding process. In some such embodiments, the container access needle 60 may be placed in a mold and subsequently a melted plastic, or other melted material, may be poured or injected into the mold and allowed to solidify to form the overmold member 62. Other processes for manufacturing the overmold member 62 are possible as well. In alternative embodiments, the overmold member 62 may be formed with a through hole or passage extending between the proximal and distal ends 65 and 66 and subsequently the container access needle 60 may be inserted into this through hole or passage. In such embodiments, the container access needle 60 may be secured to the overmold member 62 via, for example, an interference-fit connection, an adhesive, and/or a fastener.

At least the proximal end 65 of the overmold member 62 may flushly cover a length of the container access needle 60 with no gaps therebetween. As seen in FIG. 1, there may be a gap between the distal end 66 of the overmold member 62 and the container access needle 60 to form the mouth or opening for receiving the flexible tubing 52. In alternative embodiments, no mouth or opening may be formed in the distal end 66 of the overmold member 62 such that the no gap exists between the distal end 66 of the overmold member 62 and the container access needle 60.

As shown in FIG. 1, and described below in more detail with reference to FIGS. 2A-2C, prior to activation of the drug delivery device 10 (e.g., in a storage state), the overmold member 62 may define an enclosed clean space 68 between the overmold member 62 and the seal member 40. In some embodiments, the enclosed clean space 68 may be an empty space which has been sterilized and which may or may not be a vacuum. In other embodiments, the enclosed clean space may be a space filled with a gaseous or liquid sterilizing agent. In the embodiment illustrated in FIGS. 1-2C, a boundary (e.g., a sterile boundary) of the enclosed clean space 68 may be defined solely by an exterior surface 77 of the overmold member 62 and an interior surface 79 of the seal member 40. However, the boundary of the enclosed clean space 68 must not to be limited to surfaces of overmold member 62 and the seal member 40. In some embodiments, an O-ring (not illustrated) may be disposed around the proximal end 65 of the overmold member 62 such that the boundary of the enclosed clean space 68 is defined by an exterior surface of the O-ring in addition to the exterior surface 77 of the overmold member 62 and the interior surface 79 of the seal member 40. In still further embodiments, such as the one illustrated in FIGS. 3A-3C, the boundary of the enclosed clean space 68 may be defined by an interior surface of the clip member 53, an O-ring disposed around the proximal end 65 of the overmold member 62, and the distal end surface 75 of the seal member 40. Other configurations are also possible for defining the boundary of the enclosed clean space 68; however, at a minimum, the boundary of the enclosed clean space 68 may be defined by a surface of the overmold member 62 and a surface of the seal member 40.

As shown in FIGS. 1, 2B, and 3B, prior to activation of the drug delivery device 10, the container access needle 60 may be arranged in a storage position with its point 63 disposed exterior to the reservoir 30. In some embodiments, in the storage position, the point 63 of the container access needle 60 may be disposed in the enclosed clean space 68, thereby inhibiting or preventing contamination of the point 63 of the container access needle 60. In other embodiments, in the storage position, the point 63 of the container access needle 60 may be disposed partially through the seal member 40 such that the point 63 is embedded within the material of the seal member 40. Embedding the point 63 within the material of the seal member 40 may inhibit or prevent contamination of the point 63. In such embodiments, the enclosed clean space 68 may be filled with a gaseous or liquid sterilizing agent, such that during manufacturing, when the point 63 is inserted through the enclosed clean space 68, the point 63 is sterilized by the gaseous or liquid sterilizing agent.

In order to restrain the container access needle 60 in the storage position prior to activation of the drug delivery device 10, the clip member 53 may frictionally engage the exterior surface 77 of the overmold member 62. Accordingly, the clip member 53 may resist movement of the overmold member 62 in a direction toward and/or away from the seal member 40. A more detailed description of the clip member 53 is set forth.

As illustrated in FIGS. 2C and 3C, upon activation of the drug delivery device 10, the container access needle 60 may be moved from the storage position to a delivery position, where the point 63 is disposed through the proximal end surface 73 of the seal member 40 into the reservoir 30, thereby establishing fluid communication with the drug 32. In some embodiments, the actuator 28 may be mechanically linked or connected, directly or indirectly, to the container access needle 60 such that manual depression of the actuator 28 provides the motive force necessary for moving the container access needle 60 from the storage position to the delivery position 62. In other embodiments, as described above, an energized actuator (including, e.g., an electric motor, a pneumatic or hydraulic pump, and/or a source of pressurized gas or liquid) may be activated in response to a users depression of the actuator 28 and provide the motive force necessary for moving the container access needle 60 from the storage position to the delivery position.

Where appropriate, any of the above-described sub-assemblies, mechanisms, components, features, functionalities, methods of manufacture, methods of use, and other aspects of the drug delivery device 10 may be replaced with and/or combined with any of the sub-assemblies, mechanisms, components, features, functionalities, methods of manufacture, methods of use, and other aspects of the drug delivery devices described in some or all of the following documents, each of which is hereby incorporated by reference in its entirety for all purposes: U.S. Pat. No. 9,061,097; U.S. Patent Application Publication No. 2017/0124284; U.S. Patent Application Publication No. 2017/0119969; U.S. Patent Application Publication No. 2017/0098058; U.S. Patent Application Publication No. 2017/0124285; U.S. Patent Application Publication No. 2017/0103186; U.S. Provisional Patent Application No. 62/460,501 entitled "INSERTION MECHANISM FOR DRUG DELIVERY DEVICE"; U.S. Provisional Patent Application No. 62/469,226 entitled "INSERTION MECHANISM FOR DRUG DELIVERY DEVICE"; U.S. Provisional Patent Application No. 62/468,190 entitled "INSERTION MECHANISM AND METHOD OF INSERTING A NEEDLE OF A DRUG DELIVERY DEVICE"; U.S. Provisional Patent Application No. 62/460,559 entitled "DRUG DELIVERY DEVICE WITH STERILE FLUID FLOWPATH AND RELATED METHOD OF ASSEMBLY"; U.S. Provisional Patent Application No. 62/294,842 entitled "DRUG DELIVERY DEVICE, METHOD OF MANUFACTURE, AND METHOD OF USE"; U.S. Provisional Patent Application No. 62/297,718 entitled "DRUG DELIVERY DEVICE, METHOD OF MANUFACTURE, AND METHOD OF USE"; U.S. Provisional Patent Application No. 62/320,438 entitled "DRUG DELIVERY DEVICE, METHOD OF MANUFACTURE, AND METHOD OF USE"; International Patent Application No. PCT/US2017/017627 entitled "DRUG DELIVERY DEVICE, METHOD OF MANUFACTURE, AND METHOD OF USE"; and International Patent Application No. PCT/US2017/026524 entitled "DRUG DELIVERY DEVICE, METHOD OF MANUFACTURE, AND METHOD OF USE".

Turning to FIGS. 2A-2C, illustrated is an enlarged view of the container 14, the seal member 40, and the fluid pathway assembly 22 of the drug delivery device 10 shown in FIG. 1. The container 14 may have a generally cylindrical shape with an inner diameter D1. At the distal end 37 of the container 14, the wall 38 may protrude radially outwardly to define a container flange 70. The container flange 70 may extend partially or entirely around a circumference of the distal end 37 of the container 14. The container flange 70 may define a distal end surface 72 of the container 14, which is perpendicular or otherwise non-parallel to the longitudinal axis A of the container 14 and generally faces in a distal direction. The opening 45 may be formed in the distal end surface 72 and communicate with the reservoir 30 of the container 14. In some embodiments, the container flange 70 may be omitted such the distal end surface 72 does not project radially outwardly of a remainder of the container 14. The wall 38 at the proximal end 36 of the container 14 may include a proximal end surface 78, which is perpendicular or otherwise non-parallel to the longitudinal axis A of the container 14 and generally faces in a proximal direction. An opening 99 may be formed in the proximal end surface 89 and communicate with the reservoir 30. The stopper 34 may inserted through the opening 99 into the container 14 after the container 14 has been filled with the drug 32. The container 14 may be constructed of glass, plastic, or any other suitably inert material which is not likely to chemically interact with the drug 32

Referring to FIG. 2A, the seal member 40 may be centrally aligned with the longitudinal axis A of the container 14 when the seal member 40 is inserted into the container 14 such that the seal member 40 and the container 14 share the same longitudinal axis A. The seal member 40 may be divided by an imaginary plane perpendicular to the longitudinal axis A into a proximal (or bottom) end 81 and a distal (or top) end 83. The proximal end 81 and the distal end 83 may each possess a generally cylindrical shape and have outer diameters D2 and D3, respectively, as seen in FIG. 2A. The distal end 83 may be enlarged relative to the proximal end 81, such that the outer diameter D3 (or other outer dimension) of the distal end 83 is larger than an outer diameter D2 (or other outer dimension) of the proximal end 81. A flange 84 of the seal member 40 is defined by an outer peripheral (e.g., circumferential) portion of the distal end 83 of the seal member 40 that is disposed radially outwardly of the proximal end 81 of the seal member 40.

Referring to FIGS. 2B and 2C, when the seal member 40 is attached to the container 14, the proximal end 81 of the seal member 40 may be inserted through the opening 45 into the reservoir 30 and the flange 84 may directly contact and sealingly engage the distal end surface 72 of the container 14. In some embodiments, the proximal end 81 of the seal member 40 may include one or more radially outwardly protruding annular ribs 100 for sealingly engaging the inner surface 43 of the wall 38 of the container 14. The annular rib 100 may provide a secondary barrier to prevent the ingress contaminants that breach the seal between the flange 84 of the seal member 40 and the distal end surface 72 of the container 70. In embodiments including the annular rib 100, the outer diameter D2 of the proximal end 81 of the seal member 40 may be equal to or less than inner diameter D1 of the container 14. In other embodiments, the annular rib 100 may be omitted (see FIGS. 3A and 3B), and the outer diameter D2 of the proximal end 81 of the seal member 40 may be slightly larger than the inner diameter D1 of the container 14 to provide a tight fit and seal. In still further embodiments, the annular ribs 100 may be omitted and the outer diameter D2 of the proximal end 81 of the seal member 40 may be smaller than the inner diameter D1 of the container 14, such that there is not a seal formed therebetween.

Referring back to FIG. 2A, a depression or recess 80 may be formed in the seal member 40 and dimensioned to receive the proximal end 65 of the overmold member 62. The recess 80 may start at the distal end surface 75 of the seal member 40 and extend into the seal member 40 to a position which is located in the distal direction relative to the proximal end surface 73 of the seal member 40. Accordingly, the recess 80 may define a blind hole having a depth X1. The recess 80 may be defined by an interior surface 79 of the seal member 40. In some embodiments, the recess 80 may receive the overmold member 62 via an interference-fit connection (also referred to as a press-fit connection), such that the interior surface 79 of the seal member 40 sealingly engages an exterior surface 77 of the overmold member 62 to prevent or inhibit the ingress of microbes and other contaminants. The interference-fit connection may be achieved by constructing the proximal end 65 of the overmold member 62 with an outer diameter D4 (or other outer dimension) that is larger than or equal to the inner diameter D5 (or other inner dimension) of the recess 80. The interference-fit connection may result in friction between the interior surface 79 of the seal member 40 and the exterior surface 77 of the overmold member 62 that resists movement of the overmold member 62 relative to the seal member 40. In other embodiments, the outer diameter D4 of the proximal end 65 of the overmold member 62 may be smaller than the inner diameter D5 of the recess 80, and an O-ring (not illustrated) may be disposed around the proximal end 65 of the overmold member 62 to sealingly engage the interior surface 79 of the seal member 40 to prevent or inhibit the ingress of contaminants.

Referring to FIG. 2B, the enclosed clean space 68 may be formed by inserting the proximal end 65 of the overmold member 62 partially into the recess 80, such that the proximal end 65 of the overmold member 62 does not extend the entire depth X1 into the recess 80. The resulting gap between the proximal end 65 of the overmold member 62 and the bottom of the recess 80 may correspond to the enclosed clean space 68. In this way, the enclosed clean space 68 may be defined within the recess 80. In some embodiments, after insertion of the proximal end 65 of the overmold member 62 into the recess 80, the arrangement may be subjected to radiation sterilization (e.g., gamma ray sterilization or electron beam sterilization) to sterilize any residual contaminants trapped within the enclosed clean space 68.

FIG. 2B illustrates that at least a portion of the recess 80 may be disposed in a proximal direction relative to the distal end surface 72 of the container 14. Accordingly, at least a portion of the recess 80 may be disposed within the container 14. Thus, when inserted into the recess 80, at least a portion of the overmold member 62 may also be disposed within the container 14. This may reduce an axial length of the overmold member 62 which is disposed exterior to the container 14, which in turn may save space within the housing 29 of the drug delivery device 10. As a result, the drug delivery device 10 may be permitted to have a more compact design. Also a carrier assembly, described below in connection with FIG. 4, may be permitted to have a shorter axial length.

The configuration shown in FIG. 2B corresponds to a storage position or state of the container access needle 60 and the overmold member 62. The overmold member 62 may be held statically in the storage position for a period of time between the completion of assembly of the drug delivery device 10 and activation of the drug delivery device 10 by a user or patient. As shown in FIG. 2B, in the storage position, the point 63 of the container access needle 60 may be disposed in the enclosed clean space 68 and thus exterior to the reservoir 30. In other embodiments, when arranged in the storage position, the point 63 of the container access needle 60 may be disposed partially through the seal member 40 such that the point 63 is embedded within the material of the seal member 40 but nonetheless disposed exterior to the reservoir 30, as described above.

In order to prevent the tip 63 of the container access needle 60 from prematurely piercing through the seal member 40 into the reservoir 30, the clip member 53 may frictionally engage the exterior surface 77 of the overmold member 62. In some embodiments, this may be accomplished by constructing the clip member 53 with a gripping element 90 that is received in a corresponding groove 92 formed in the exterior surface 77 of the overmold member 62 in the storage state, as shown in FIG. 2B. Friction between the gripping element 90 and the groove 92 may advantageously resist movement of the overmold member 62, and thus the container access needle 60, toward and/or away from the seal member 40 prior to use of the drug delivery device 10. Upon activation of the drug delivery device 10, an actuator (e.g., the actuator 28 or an internal energized actuator) may be configured to exert a motive force overcoming the frictional force between the gripping element 90 and the groove 92, and also any frictional force between the overmold member 62 and the interior surface 79 of the seal member 40 if an interference-fit connection exists therebetween, to cause the gripping element 90 to slide out of the groove 92 and move the overmold member 62 from the storage position (FIG. 2B) to the delivery position (FIG. 2C). As a result, the point 63 of the container access needle 60 may pierce through the proximal end surface 73 of the seal member 40 into the reservoir 30, thereby establishing fluid communication with the drug 32.

In the present embodiment, the gripping element 90 may be configured as a continuous annular ridge or protrusion. In other embodiments, multiple, distinct gripping elements may be formed on the clip member 53, each of which may be received in a corresponding groove formed in the exterior surface 77 of the overmold member 62 in the storage state.

Referring back to FIG. 2A, the clip member 53 may have an interior surface 94 defining a through hole 95. The through hole 95 may extend between a proximal end surface 96 and a distal end surface 97 of the clip member 53. The proximal end surface 96 of the clip member 53 may be disposed in direct contact with the distal end surface 75 of the seal member 40. The overmold member 62 may extend entirely through the through hole 95 when assembled to the clip member 53, as illustrated in FIGS. 2B and 2C. The gripping element 90 may be disposed on or formed by the interior surface 94, such that the gripping element 90 extends radially inwardly into the through hole 95.

As illustrated in FIGS. 2B and 2C, a fastener 91 may be configured to hold or clamp the clip member 53 to the container 14, with the seal member 40 positioned between clip member 53 and the container 14. In some embodiments, the fastener 91 may take the form of a crimp ring that is applied to the container 14 and clip member 53 with a crimping tool. As shown in FIGS. 2B and 2C, the fastener 91 may include radially inwardly extending flanges 93a and 93b that abut against, respectively, a proximally facing surface of the container flange 70 (or other exterior surface of the wall 38 of the container 14) and the distal and surface 97 of the clip member 53, in order to clamp or press the proximal end surface 90 of the flange 84 of the seal member 40 tightly against the distal end surface 72 of the container 70. The clamping force provided by the fastener 94 may help ensure an air-tight and/or fluid-tight seal between the flange 84 of the seal member 40 and the distal end surface 72 of the container 70.

In each of the foregoing embodiments, the enclosed clean space is formed by inserting the overmold member into a recess in the seal member. However, the enclosed clean space may be achieved through other configurations as well. FIGS. 3A-3C illustrate an embodiment where the clip member defines a portion of the boundary of the enclosed clean space between the overmold member and the seal member. Elements of the assembly depicted in FIGS. 3A-3C which are similar to those shown in FIGS. 1-2C are designated by the same reference numeral, incremented by 100. A description of many of these elements is abbreviated or even eliminated in the interest of brevity.

Referring to FIG. 3A, the seal member 140 may be similar in construction to the above-described seal member 40, except that the seal member 140 does not include a recess formed in its distal end surface 175. Rather, the distal end surface 175 may extend between opposite lateral sides of the seal member 140 and may be planar or substantially planar. The lack of a recess formed in the distal end surface 175 may simplify the manufacturing of the seal member 140 and/or allow the seal member 140 to be used in combination with a variety of standard container designs. In alternative embodiments, the seal member 140 may have a recess similar to the recess 80 formed in the seal member 40. Though the seal member 140 may not include a recess formed in its distal end surface 175, the seal member 140 may have a recess 250 formed in its proximal end surface 173 for HUV control, as shown in FIG. 3A.

With continued reference to FIG. 3A, the clip member 153 may include an interior surface 194 defining a through hole 195. The through hole 195 may extend between a proximal end surface 196 and a distal end surface 197 of the clip member 153. The proximal end surface 196 of the clip member 153 may be disposed in direct contact with the distal end surface 175 of the seal member 140, and sealingly engage the distal end surface 175 of the seal member 140 with the aid of the clamping force provided by the fastener 191.

In some embodiments, a proximal end 210 of the clip member 153 may include a flange 211 that extends radially outwardly of a distal end 212 of the clip member 153, such that an outer diameter (or other outer dimension) of the proximal end 210 is larger than an outer diameter (or other outer dimension) of the distal end 212. Furthermore, in some embodiments, the proximal end 210 of the clip member 153 generally may have the shape of a flattened disk for increasing the surface area of the proximal end surface 196 in contact with the distal end surface 175 of the seal member 140 to promote sealing, whereas the distal end 212 of the clip member 153 generally may have the shape of an elongated tubular member so that the length of the through hole 195 is sufficient to create the enclosed clean space 168 for accommodating the point 163 of the container access needle 160. Accordingly, an axial length of the distal end 212 of the clip member 153 may be longer than that of the proximal end 210 of the clip member 153. The through hole 195 may extend as a continuous passage through the proximal end 210 and the distal end 212 of the clip member 153.

Referring still to FIG. 3B, the enclosed clean space 168 may be formed by inserting the proximal end 165 of the overmold member 162 partially through the through hole 195 of the clip member 153, such that the proximal end 165 of the overmold member 162 extends into the through hole 195 and terminates within the through hole 195. The resulting gap between the proximal end 165 of the overmold member 162 and the distal end surface 175 of the seal member 140 may correspond to the enclosed clean space 168. In this way, the enclosed clean space 168 may be defined within the through hole 195. In some embodiments, after partial insertion of the proximal end 165 of the overmold member 162 into the through hole 195, the arrangement may be subjected to a radiation sterilization treatment (e.g., gamma ray sterilization or electron beam sterilization) to sterilize any residual contaminants trapped within the enclosed clean space 168.

Still referring to FIG. 3B, an O-ring 220 may be disposed around the proximal end 165 of the overmold member 162. The O-ring 220 may be configured to sealingly and slidably engage the interior surface 194 of the through hole 195. Accordingly, a boundary (e.g., a sterile boundary) of the enclosed clean space 168 may be defined by the exterior surface of the of the O-ring 220, the exterior surface 177 of the overmold member 162, the interior surface 194 of the clip member 153, and the distal end surface 175 of the seal member 140. In alternative embodiments, the O-ring 220 may be omitted, and instead the through hole 195 of the clip member 153 may receive the proximal end 165 of the overmold member 162 via an interference-fit connection. In such embodiments, the boundary of the enclosed clean space 168 may be defined solely by the exterior surface 177 of the overmold member 162, the interior surface 194 of the clip member 153, and the distal end surface 175 of the seal member 140. Other configurations are also possible for defining the boundary of the enclosed clean space 168; however, at a minimum, the boundary of the enclosed clean space 168 may be defined by the exterior surface 177 of the overmold member 162, the interior surface 194 of the clip member 153, and the distal end surface 175 of the seal member 140.

The configuration shown in FIG. 3B corresponds to a storage position or state of the container access needle 160 and the overmold member 162. The overmold member 162 may be held statically in the storage position for a period of time between the completion of assembly of the drug delivery device 10 and activation of the drug delivery device 10 by a user or patient. As shown in FIG. 3B, in the storage position, the point 163 of the container access needle 160 may be disposed in the enclosed clean space 168 and thus exterior to the reservoir 130. In other embodiments, when arranged in the storage position, the point 163 of the container access needle 160 may be disposed partially through the seal member 140 such that the point 163 is embedded within the material of the seal member 140 but nonetheless disposed exterior to the reservoir 130.

In order to prevent the tip 163 of the container access needle 160 from prematurely piercing through the seal member 140 into the reservoir 130, the clip member 153 may frictionally engage the exterior surface 177 of the overmold member 162. In some embodiments, this may be accomplished by constructing the clip member 153 with a gripping element 190 that is received in a corresponding groove 192 formed in the exterior surface 177 of the overmold member 162 in the storage state, as shown in FIG. 3B. The gripping element 190 may be disposed on or formed by the interior surface 194, such that the gripping element 190 extends radially inwardly into the through hole 195. Friction between the gripping element 190 and the groove 192 may resist movement of the overmold member 162, and thus the container access needle 160, toward and/or away from the seal member 140 prior to use of the drug delivery device 10. Upon activation of the drug delivery device 10, an actuator (e.g., the actuator 28 or an internal energized actuator) may be configured to exert a motive force overcoming the frictional force between the gripping element 190 and the groove 192 to cause the gripping element 190 to slide out of the groove 192 and move the overmold member 162 from the storage position (FIG. 3B) to the delivery position (FIG. 3C). As a result, the point 163 of the container access needle 60 may pierce through the proximal end surface 173 of the seal member 140 into the reservoir 130, thereby establishing fluid communication with the drug 132.

In the present embodiment, the gripping element 190 may be configured as a continuous annular ridge or protrusion. In other embodiments, the gripping element 190 may be formed by with multiple, distinct gripping elements, each of which may be received in a corresponding groove formed in the in the exterior surface 177 of the overmold member 162 in the storage state. In addition to the gripping element 190, the clip member 153 may include a gripping element 221 located at an axial position which is located in the proximal direction relative to the gripping element 190. The gripping element 221 may be disposed on or formed by the interior surface 194, such that the gripping element 221 extends radially inwardly into the through hole 195. The gripping element 221 may be received in the groove 192 formed in the exterior surface 177 of the overmold member 162 in the delivery state, as shown in FIG. 3C. Friction between the gripping element 221 and the groove 192 may advantageously resist movement of the overmold member 162, and thus the container access needle 160, toward and/or away from the seal member 140 during and after delivery of the drug 132.

The clip members 53 and 153 may be constructed of any suitably rigid or semi-rigid material including, for example, plastic and/or metal.

The fluid pathway assemblies described in connection with FIGS. 2A-3C advantageously permit a thinner construction of the flange (84 or 184) located at the distal end of the seal member. This is because the distal end of the seal member is not the sole element responsible for defining the enclosed clean space for the tip of the container access needle. Rather, the enclosed clean space can be defined by a portion of the seal member located within the container (FIGS. 2A-2C) and/or defined by a clip member positioned exterior to the seal member (FIGS. 3A-3C). As a consequence, the thickness of the flange at the distal end of the seal member can be reduced. This, in turn, facilitates sterilization of the interface between proximal end surface of the seal member and the distal end surface of the container. A thinner flange means that proximally-directed sterilization beams (e.g., electron beams or gamma rays) are required to penetrate through less seal member material in order to reach the interface. Lower energy sterilization beams may be used as a result, which reduces the possibility of discoloration of the material used to construct the container and/or reduces manufacturing costs.

Methods of assembling the drug delivery device 10 will now be described. The following methods of assembly are described in the context of the embodiment illustrated in FIGS. 2A-2C, but also apply the embodiment illustrated in FIGS. 3A-3C unless noted otherwise. The assembly process may take place in at least two distinct stages: an initial stage where a sterile fluid flow path is established between the container 14 and the needle insertion mechanism 12 and the container 14 is filled with the drug 32; and a final assembly stage where the pre-filled container 14 and the components previously attached thereto are installed in the drug delivery device 10. The initial stage and the final assembly stage may be performed by separate manufacturers and/or in separate facilities. For instance, the initial stage may be performed by the drug manufacturer, whereas the final assembly stage may be performed by the device manufacturer.

The initial stage may involve initially providing an empty container 14, and covering the opening 45 of the container 14 with the seal member 40. In this step, the proximal end 81 of the seal member 40 may be inserted into the container 14 until the flange 84 abuts against the distal end surface 72 of the container. Next, the clip member 53 may be disposed on the seal member 40, such that the proximal end surface 81 of the seal member 40 directly contacts the distal end surface 75 of the seal member 40. Then, the fastener 91 may be applied to the exterior surface of the clip member 53 and the exterior surface 47 of the wall 38 of the container 14 to secure the clip member 53 to the container 14 with the seal member 40 positioned between the clip member 53 to the container 14. A clamping force provided by the fastener may form of a seal between the seal member 40 and distal end surface 72 of the container and/or between the seal member 40 and the proximal end surface 96 of the clip member 53.

Next, the proximal end 65 of the overmold member 62 may be inserted through the through hole 95 in the clip member 53 and partially into the recess 80 to define the enclosed clean space 68 between the overmold member 62 and the seal member 62. The proximal end 65 of the overmold member 62 may be inserted through the through hole 95 until the gripping element 90 is received in the corresponding groove 92 formed in the exterior surface 77 of the overmold member 62, thereby frictionally locking the overmold member 62 relative to the clip member 53. After this step, the point 63 of the container access needle 60 may be either disposed in the enclosed clean space 68 or embedded within the material of the seal member 40. In alternative embodiments, the proximal end 65 of the overmold member 62 may be inserted through the through hole 95 in the clip member 53 prior to attachment of the clip member 53 to the seal member 40. When the clip member 53 is later attached to the seal member 40, the proximal end 65 of the overmold member 62 may then be partially inserted into the recess 80 to define the enclosed clean space 68 between the overmold member 62 and the seal member 62.

Assembly of the container 114, the overmold member 162, and the clip member 153 may be similar to the steps described in the preceding paragraph, except that the overmold member 162 may be inserted only partially through the through hole 195. As a result, a terminal or proximal end 165 of the overmold member 62 may be disposed within the through hole 195.

Figure 4:
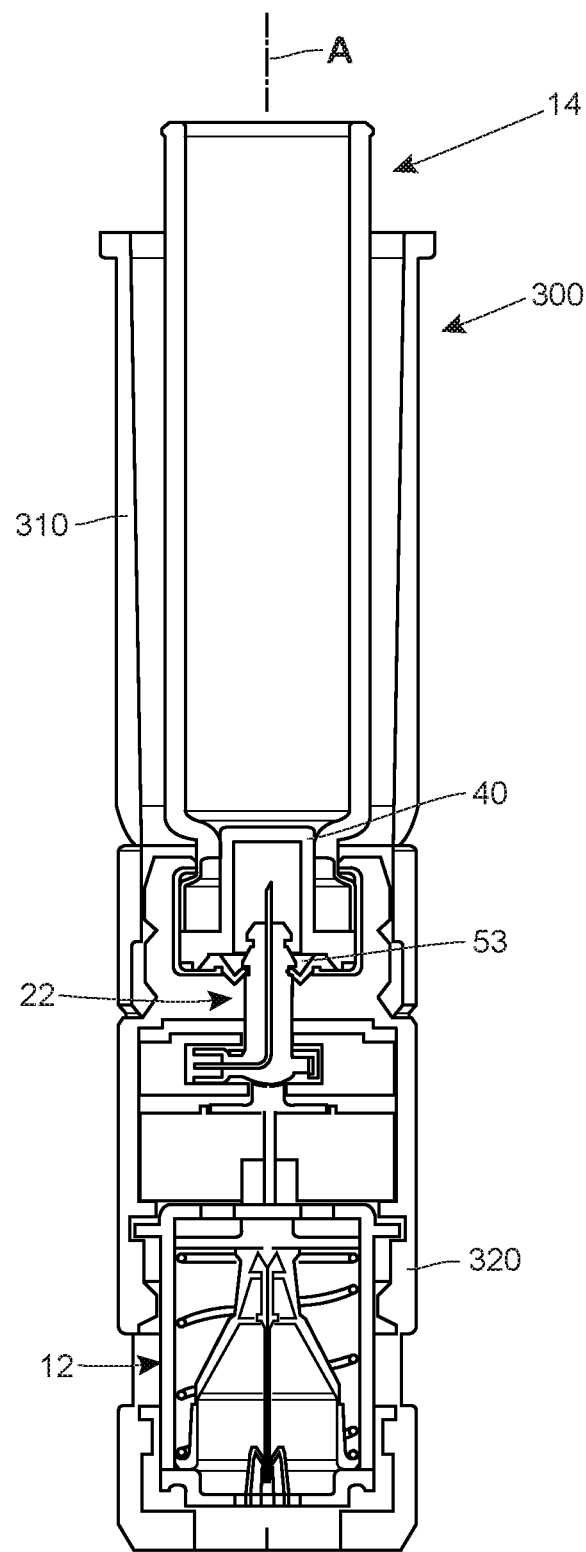
FIG. 4 illustrates an embodiment of a carrier assembly in accordance with the present disclosure.

Subsequently, the container 14 and the attached fluid pathway assembly 22 may be removably connected to the needle insertion mechanism 12 via a carrier assembly 300, as shown in FIG. 4. This may involve inserting the container 114 into a hollow sleeve 310 of the carrier assembly 300 such that the hollow sleeve 310 is disposed the container, and inserting the needle insertion mechanism 12 into a hollow carrier element 320 such that the carrier element 320 is disposed around the insertion mechanism 12. Next, an end of the carrier element 320 may be inserted into and removably connected to an interior surface of sleeve 310. Additionally, this process may involve connecting the flexible tubing 52 (not shown in FIG. 4) to the distal end 66 of the overmold member 62 and/or an inlet port of the insertion mechanism 12. When assembled within the carrier assembly 300, the insertion mechanism 12 may have its longitudinal axis aligned with or parallel to the longitudinal axis A of the container 14, which may render the arrangement suitable for standard filling and capping machines. Subsequently, the arrangement of the carrier assembly 300, the container 14, the fluid pathway assembly 22, and the insertion mechanism 12 may be subjected to a sterilization treatment, including, but not limited to, radiation sterilization treatments (utilizing, e.g., gamma rays, e-rays, and/or electron beams) and/or gaseous sterilization treatments (utilizing, e.g., ethylene oxide, ozone, chlorine dioxide, nitrogen dioxide, and/or steam). This may help ensure the sterility of the fluid flow path between the container 14 and the insertion mechanism 12.

After sterilization, the reservoir 30 of the container 14 may be filled with a volume of the drug 32 and then the stopper 34 may be inserted through the opening 99 of container 14 to seal close the proximal end 36 of the container 14. This filling and capping procedure may be carried out in a sterile or aseptic environment. Furthermore, the container 14 may be disposed within the carrier assembly 300 throughout this filling and capping procedure.

Subsequently, the filled container 14, along with the attached carrier assembly 300, fluid pathway assembly 22, and insertion mechanism 12, may be packaged and shipped to a facility where the final assembly of the drug delivery device 10 is to occur.

At the final assembly facility, the carrier assembly 300 may be removed from the container 14, the fluid pathway assembly 22, and the insertion mechanism 12 and these components may be installed within the housing 29 of the drug delivery device 10 along with other components and sub-assemblies of the drug delivery device 10. At the completion of the final assembly stage, the drug delivery device 10 may be configured as a pre-loaded and pre-filled drug delivery device.

Drug Information

As mentioned above, the container may be filled with a drug. This drug may be any one or combination of the drugs listed below, with the caveat that the following list should neither be considered to be all inclusive nor limiting.

For example, the syringe may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the syringe may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP⁻; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present disclosure are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACl-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100);

anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. Nos. 8,030,547, 8,563,698, 8,829,165, 8,859,741, 8,871,913, 8,871,914, 8,883,983, 8,889,834, 8,981,064, 9,056,915, 8,168,762, 9,045,547, 8,030,457, 8,030,457, 8,829,165, 8,981,064, 8,030,457, U.S. Publication No. 2013/0064825, U.S. Patent Application Publication No. 2012/0093818, U.S. Patent Application Publication No. 2013/0079502, U.S. Patent Application Publication No. 2014/0357850, U.S. Patent Application Publication No. 2011/0027287, U.S. Patent Application Publication No. 2014/0357851, U.S. Patent Application Publication No. 2014/0357854, U.S. Patent Application Publication No. 2015/0031870, U.S. Patent Application Publication No. 2013/0085265, U.S. Patent Application Publication No. 2013/0079501, U.S. Patent Application Publication No. 2012/0213797, U.S. Patent Application Publication No. 2012/0251544, U.S. Patent Application Publication No. 2013/0072665, U.S. Patent Application Publication No. 2013/0058944, U.S. Patent Application Publication No. 2013/0052201, U.S. Patent Application Publication No. 2012/0027765, U.S. Patent Application Publication No. 2015/0087819, U.S. Patent Application Publication No. 2011/0117011, U.S. Patent Application Publication No. 2015/0004174, U.S. Provisional Patent Application No. 60/957,668, U.S. Provisional Patent Application No. 61/008,965, U.S. Provisional Patent Application No. 61/010,630, U.S. Provisional Patent Application No. 61/086,133, U.S. Provisional Patent Application No. 61/125,304, U.S. Provisional Patent Application No. 61/798,970, U.S. Provisional Patent Application No. 61/841,039, U.S. Provisional Patent Application No. 62/002,623, U.S. Provisional Patent Application No. 62/024,399, U.S. Provisional Patent Application No. 62/019,729, U.S. Provisional Patent Application No. 62/067,637, U.S. patent application Ser. No. 14/777,371, International Patent Application No. PCT/US2013/048714, International Patent Application No. PCT/US2015/040211, International Patent Application No. PCT/US2015/056972, International Patent Application Publication No. WO/2008/057457, International Patent Application Publication No. WO/2008/057458, International Patent Application Publication No. WO/2008/057459, International Patent Application Publication No. WO/2008/063382, International Patent Application Publication No. WO/2008/133647, International Patent Application Publication No. WO/2009/100297, International Patent Application Publication No. WO/2009/100318, International Patent Application Publication No. WO/2011/037791, International Patent Application Publication No. WO/2011/053759, International Patent Application Publication No. WO/2011/053783, International Patent Application Publication No. WO/2008/125623, International Patent Application Publication No. WO/2011/072263, International Patent Application Publication No. WO/2009/055783, International Patent Application Publication No. WO/2012/0544438, International Patent Application Publication No. WO/2010/029513, International Patent Application Publication No. WO/2011/111007, International Patent Application Publication No. WO/2010/077854, International Patent Application Publication No. WO/2012/088313, International Patent Application Publication No. WO/2012/101251, International Patent Application Publication No. WO/2012/101252, International Patent Application Publication No. WO/2012/101253, International Patent Application Publication No. WO/2012/109530, and International Patent Application Publication No. WO/2001/031007, International Patent Application Publication No. WO/2009/026558, International Patent Application Publication No. WO/2009/131740, International Patent Application Publication No. WO/2013/166448, and International Patent Application Publication No. WO/2014/150983.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the drug comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the drug comprises a therapeutically effective amount of the anti-TSLP antibody designated as A5 within U.S. Pat. No. 7,982,016.

While the present disclosure has been described in connection with various embodiments, it will be understood that the present disclosure is capable of further modifications. The present disclosure is intended to cover any variations, uses, or adaptations of the disclosed subject matter following, in general, the principles of the present disclosure, and including such departures from the present disclosure as, within the known and customary practice within the art to which the present disclosure pertains.

It is noted that the construction and arrangement of the drug delivery device and its various components and assemblies as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure.

What is claimed is:

1. A drug delivery device comprising:
   a housing having an opening;
   a container disposed at least partially within the housing and including a wall with an interior surface and a seal member with an end surface, the interior surface of the wall and the end surface of the seal member defining a reservoir filled with a drug, wherein a position of the seal member is fixed with respect to a position of the wall of the container;
   a delivery member having an initial position wherein a distal end of the delivery member is disposed within the housing and a second position wherein at least the distal end of the delivery member is disposed through the opening for insertion into a patient; and
   a fluid pathway assembly connected to the container and including:
     a container access needle having a point, and
     an overmold member covering a length of the container access needle, the overmold member being moveable relative to the seal member to carry the container access needle between a storage position, where the point is disposed exterior to the reservoir, and a delivery position, where the point extends through the end surface of the seal member into the reservoir,
     wherein during drug delivery the overmold member facilitates fluid communication between the container access needle and the delivery member.

2. The drug delivery device of claim 1, comprising an enclosed spaced disposed at least partially between the overmold member and the seal member, and wherein the point of the container access needle is disposed in the enclosed space when the container access needle is disposed in the storage position.

3. The drug delivery device of claim 1, comprising:
   an enclosed spaced disposed at least partially between the overmold member and the seal member; and
   a recess formed in the seal member and receiving a proximal end of the overmold member, wherein the enclosed space is defined within the recess.

4. The drug delivery device of claim 3, the recess receiving the proximal end of the overmold member via an interference-fit connection.

5. The drug delivery device of claim 4, a proximal end of the seal member extending into the container such that at least a portion of the recess is disposed within the container.

6. The drug delivery device of claim 1, comprising a clip member mounted on the seal member and frictionally engaging the overmold member to resist movement of the overmold member relative to the seal member.

7. The drug delivery device of claim 6, the clip member having an interior surface defining a through hole, the proximal end of the overmold member extending through the through hole and into a recess formed in the seal member.

8. The drug delivery device of claim 6, the interior surface of the clip member defining a gripping element, the gripping element being received in a corresponding groove formed in the overmold member when the container access needle is disposed in the storage position.

9. The drug delivery device of claim 1, comprising:
   an enclosed spaced disposed at least partially between the overmold member and the seal member; and
   a clip member mounted on the seal member and frictionally engaging the overmold member to resist movement of the overmold member relative to the seal member, the clip member having an interior surface defining a through hole, a proximal end of the overmold member extending partially through the through hole, wherein the enclosed spaced is defined within the through hole.

10. The drug delivery device of claim 9, comprising an O-ring disposed about the proximal end of the overmold member and sealingly and slidably engaging the interior surface of the clip member.

11. The drug delivery device of claim 9, the clip member having a proximal end and a distal end, the proximal end including a mounting flange disposed radially outwardly of the distal end and engaging the seal member.

12. The drug delivery device of claim 9, the interior surface of the clip member defining a gripping element, the gripping element being received in a corresponding groove formed in the overmold member when the container access needle is disposed in the storage position.

13. The drug delivery device of claim 1, wherein the overmold member is configured to move relative to the wall of the container to carry the container access needle between the storage position and the delivery position.

14. A method of assembly comprising:
   providing a housing having an opening;
   providing a delivery member having an initial position wherein a distal end of the delivery member is disposed within the housing and a second position wherein at least the distal end of the delivery member is disposed through the opening for insertion into a patient;

providing a container configured to be disposed at least partially within the housing and having a wall with an interior surface, and a fluid pathway assembly including a container access needle having a point and an overmold member, the overmold member covering a length of the container access needle with the point protruding outwardly from the overmold member, the overmold member during drug delivery facilitating fluid communication between the container access needle and the delivery member;

covering a first opening formed in the wall of the container with a seal member such that an end surface of the seal member and the interior surface of the wall of the container define a reservoir, wherein a position of the seal member is fixed with respect to a position of the wall of the container.

15. The method of claim 14, comprising mounting a clip member on the seal member and frictionally engaging the clip member and the overmold member.

16. The method of claim 15, wherein frictionally engaging the clip member and the overmold member includes aligning an inwardly protruding gripping element of the clip member with a corresponding groove formed in the overmold member such that the inwardly protruding gripping element is received in the corresponding groove.

17. The method of claim 14, comprising inserting the overmold member into a recess formed in the seal member to at least partially define an enclosed space between the overmold member and the seal member.

18. The method of claim 17, wherein inserting the overmold member into the recess formed in the seal member includes forming an interference-fit connection between the overmold member and the seal member.

19. The method of claim 15, comprising partially inserting the overmold member through a through hole of the clip member such that a terminal end of the overmold member is disposed within the through hole.

20. The method of claim 19, comprising sealingly engaging an interior surface of the clip member with an O-ring disposed around the terminal end of the overmold member.

21. The method of claim 14, comprising filling the reservoir of the container with a drug.

22. The method of claim 14, wherein the overmold member is configured to move relative to the wall of the container to carry the container access needle between the storage position and the delivery position.

* * * * *